United States Patent
Yamamoto et al.

(10) Patent No.: US 9,995,717 B2
(45) Date of Patent: Jun. 12, 2018

(54) OBJECT INFORMATION ACQUIRING APPARATUS AND OBJECT INFORMATION ACQUIRING METHOD

(71) Applicant: CANON KABUSHIKI KAISHA, Tokyo (JP)

(72) Inventors: Hiroshi Yamamoto, Kawasaki (JP); Yukio Furukawa, Sagamihara (JP); Toshinobu Tokita, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 325 days.

(21) Appl. No.: 14/794,441

(22) Filed: Jul. 8, 2015

(65) Prior Publication Data
US 2015/0335251 A1 Nov. 26, 2015

Related U.S. Application Data

(62) Division of application No. 13/600,399, filed on Aug. 31, 2012, now Pat. No. 9,116,110.

(30) Foreign Application Priority Data

Sep. 8, 2011 (JP) ................................. 2011-196049

(51) Int. Cl.
*G01N 29/09* (2006.01)
*A61B 5/145* (2006.01)
(Continued)

(52) U.S. Cl.
CPC ....... *G01N 29/2418* (2013.01); *A61B 5/0095* (2013.01); *A61B 5/14542* (2013.01);
(Continued)

(58) Field of Classification Search
CPC .............. A61B 5/0095; A61B 5/14542; A61B 2576/00; G01N 29/2418; G01N 29/09; G01N 29/06; G01N 2291/02466
(Continued)

(56) References Cited

U.S. PATENT DOCUMENTS

| | | | |
|---|---|---|---|
| 7,861,574 B2 * | 1/2011 | Sheen ................ | G01N 21/1702 73/24.02 |
| 7,867,167 B2 * | 1/2011 | Boctor ..................... | A61B 8/00 600/437 |

(Continued)

FOREIGN PATENT DOCUMENTS

| JP | S60-021744 | 2/1985 |
|---|---|---|
| JP | S60-021774 | 2/1985 |

(Continued)

OTHER PUBLICATIONS

Office Action dated Apr. 28, 2015 in counterpart Japanese patent application 2011-196049, with translation.

(Continued)

*Primary Examiner* — J M Saint Surin
(74) *Attorney, Agent, or Firm* — Fitzpatrick, Cella, Harper & Scinto

(57) ABSTRACT

This invention employs an object information acquiring apparatus including a probe for receiving, as a received signal, an acoustic wave which is generated within an object irradiated with light and propagates on an object surface, and a processor for generating object information, which is information based on an internal optical characteristic value of the object, by using intensity of the received signal. The processor corrects the intensity of the received signal by using the reflectance upon the acoustic wave entering the probe which is calculated based on the angle of the acoustic (Continued)

wave entering the probe, and on the acoustic impedance and acoustic velocity of the object and the probe.

36 Claims, 14 Drawing Sheets

(51) Int. Cl.
    *A61B 5/00*     (2006.01)
    *G01N 29/24*     (2006.01)
    *G01N 29/06*     (2006.01)

(52) U.S. Cl.
    CPC .......... *G01N 29/09* (2013.01); *A61B 2576/00* (2013.01); *G01N 29/06* (2013.01); *G01N 2291/02466* (2013.01)

(58) Field of Classification Search
    USPC ........................................................ 73/602
    See application file for complete search history.

(56) References Cited

U.S. PATENT DOCUMENTS

| | | | | |
|---|---|---|---|---|
| 8,276,452 | B2* | 10/2012 | Takeishi | G01N 29/2418 73/596 |
| 2006/0079780 | A1 | 4/2006 | Karasawa | 600/447 |
| 2009/0293621 | A1* | 12/2009 | Kitazawa | G01N 29/06 73/606 |
| 2010/0191109 | A1 | 7/2010 | Fukutani et al. | 600/437 |
| 2011/0208057 | A1 | 8/2011 | Oikawa | 600/443 |
| 2011/0230762 | A1 | 9/2011 | Tokita et al. | 600/437 |
| 2011/0245667 | A1 | 10/2011 | Tokita | 600/437 |
| 2011/0251475 | A1 | 10/2011 | Tokita et al. | 600/407 |
| 2011/0270071 | A1 | 11/2011 | Furukawa | 600/407 |
| 2011/0303015 | A1 | 12/2011 | Ichihara et al. | 73/656 |
| 2012/0150012 | A1 | 6/2012 | Fujimoto et al. | 600/407 |
| 2012/0167694 | A1 | 7/2012 | Li | 73/657 |
| 2012/0183190 | A1 | 7/2012 | Fukutani et al. | 382/182 |
| 2012/0238859 | A1 | 9/2012 | Tokita et al. | 600/407 |
| 2012/0302865 | A1 | 11/2012 | Tokita et al. | 600/407 |
| 2013/0085371 | A1 | 4/2013 | Miyasato | 600/407 |
| 2013/0160559 | A1 | 6/2013 | Ichihara et al. | 73/655 |
| 2014/0114170 | A1 | 4/2014 | Tokita et al. | 600/407 |

FOREIGN PATENT DOCUMENTS

| | | |
|---|---|---|
| JP | H03-125962 | 5/1991 |
| JP | 2006-095000 | 4/2006 |
| JP | 2010-167258 | 8/2010 |
| JP | 2011-120765 | 6/2011 |

OTHER PUBLICATIONS

M. Ito et al., "Ultrasound Diagnostic Equipment," Corona Publishing Co. Ltd., Japan, Aug. 26, 2002, pp. 44-45 (with translation).

* cited by examiner

| PROPAGATING MEDIUM | ACOUSTIC IMPEDANCE ($\times 10^6 kg/m^2 s$) |
|---|---|
| LUNG | 0.62 |
| FAT | 1.35 |
| WATER | 1.52 |
| BLOOD | 1.62 |
| LIVER | 1.64–1.68 |
| MUSCLE | 1.65–1.67 |
| BRAIN | 1.55–1.66 |
| SPLEEN | 1.65–1.67 |
| KIDNEY | 1.62 |
| BONE | 3.75–7.83 |

FIG. 12

OBJECT INFORMATION ACQUIRING APPARATUS AND OBJECT INFORMATION ACQUIRING METHOD

RELATED APPLICATIONS

This application is a divisional application of application Ser. No. 13/600,399, filed Aug. 31, 2012. It claims benefit of that application under 35 U.S.C. § 120, and claims benefit under 35 U.S.C. § 119 of Japanese Patent Application No. 2011-196049, filed on Sep. 8, 2011. The entire contents of each of the mentioned prior applications are incorporated herein by reference.

BACKGROUND OF THE INVENTION

Field of the Invention

This invention relates to an object information acquiring apparatus and an object information acquiring method.

Description of the Related Art

The research of optical imaging technology capable of obtaining information in a living subject by irradiating light to the living subject from a light source such as a laser is being actively pursued in the medical field. Photoacoustic Tomography (PAT) is one of the optical imaging technologies. A photoacoustic tomography device irradiates pulsed light generated from the light source to the living subject, and uses a probe to receive, in various positions, an acoustic wave (typically an ultrasound wave) that is generated when the body tissue, which absorbed the light energy that propagated and diffused in the living subject, instantaneously expands. It is thereby possible to detect, for instance, the difference in the absorption factor of light energy in the suspected site of a tumor or the like and other tissues.

Subsequently, the image reconfiguration region (region where information in the living subject is to be imaged) is divided into a plurality of voxels or pixels. In addition, image reconfiguration is performed by using the received signal of the timeframe in which the acoustic wave reaches the elements of the probe from the voxels or pixels. For the image reconfiguration process, FBP (Filtered Backprojection), DELAY-AND-SUM and other well-known methods may be used. It is thereby possible to obtain the optical characteristic value distribution such as the initial sound pressure distribution or the absorption coefficient distribution in the living subject. As a result of performing photoacoustic measurement using light of various wavelengths, it is possible to quantitatively observe a specific substance in the object; for example, measure the hemoglobin concentration contained in the blood or measure the oxygen saturation of the blood.

In Photoacoustic Tomography, a probe is used to receive the acoustic wave. In the field of ultrasound diagnostic devices that similarly receive acoustic waves using a probe, it is known that the receiving sensitivity of the probe depends on the incidence angle of the acoustic wave that enters the probe (NPL 1: "Ultrasound Wave Diagnostic Device" Co-authored by Masayasu Ito and Tsuyoshi Mochizuki, Published by Corona Publishing Co., Ltd., Aug. 26, 2002). In other words, as the incidence angle of the acoustic wave that enters the probe increases, the receiving sensitivity of the probe decreases, and there is a problem in that imaging of favorable directionality cannot be performed.

Thus, Japanese Patent Application Publication No. S60-021744 (PTL 1) discloses a method of correcting the differences in the receiving sensitivity caused by the incidence angle. In PTL 1, the probe transmits the acoustic wave at a certain angle, and receives the reflected wave from the object. In addition, the sensitivity difference which arises according to the incidence angle of the acoustic wave is corrected by changing the amplification factor for each element of the probe, and the sensitivity of the respective elements is caused to be uniform so as to enable imaging of favorable directionality.

Patent Literature 1 (PTL 1): Japanese Patent Application Publication No. S60-021744

Non Patent Literature 1 (NPL 1): "Ultrasound Wave Diagnostic Device" Co-authored by Masayasu Ito and Tsuyoshi Mochizuki, Published by Corona Publishing Co., Ltd., Aug. 26, 2002

SUMMARY OF THE INVENTION

In the field of Photoacoustic Tomography also, there is a problem in that the receiving sensitivity of the probe differs depending on the incidence angle of the acoustic wave. Even when acoustic waves having the same intensity are used, the acoustic wave is detected to be smaller when the acoustic wave enters the probe diagonally in comparison to a case where the acoustic wave enters the probe perpendicularly. Thus, the visual angle (aperture angle) from the arbitrary voxel or pixel to the element apparently decreases. When the aperture angle decreases, the resolution of the reconstructed image will deteriorate. Based on the principle of Photoacoustic Tomography, while it is ideal to reconfigure the image by receiving acoustic waves at all circumferences of the light absorber so as to accurately learn the size of the light absorber, the reconstructed image will become blurry when the range of receiving the acoustic waves is limited.

To deal with this problem, the field of ultrasound wave diagnosis employs the method of PTL 1. Nevertheless, with Photoacoustic Tomography, since it is not possible to know from which angle the acoustic wave was propagated when acoustic wave is received, it is not possible to use the method of PTL 1. Even if the method of PTL 1 is applied to Photoacoustic Tomography, it would be inappropriate since signals other than those of a timeframe in which signals should be received from the voxels or pixels to be subject to image reconfiguration are also amplified.

Moreover, the sensitivity of the probe is determined based on the aperture of the probe and the reflectance loss on the probe surface. Here, the relationship of the aperture of the probe and the reflectance loss on the probe surface is explained.

Foremost, FIG. 12 shows a table of the acoustic impedance of the body tissues (Source: NPL 1, p. 13, Table 2.1). As evident from this table, the acoustic impedance of body tissues differs based on the propagating medium.

FIG. 10 is a combination of a graph (solid line) showing the relationship of the incidence angle of the acoustic wave entering the probe and the transmittance of the acoustic wave into the probe, and a graph (respective dotted lines) showing the relationship of the incidence angle of the acoustic wave entering the probe and the receiving sensitivity of the probe for each element size of the probe. Here, the acoustic wave frequency was set to 1 MHz. The additional settings were as follows; namely, the acoustic impedance $Z_1$ of the object=$1.5 \times 10^6$ kg/m²s, the acoustic velocity $c_1$ of the object=1500 m/s, the acoustic impedance $Z_2$ of the probe (acoustic matching layer of the probe surface)=$1.8 \times 10^6$ kg/m²s, and the acoustic velocity $c_2$ of the probe=2100 m/s.

Upon viewing the graph, when the element size of the probe is 1 mm or more, the deterioration in sensitivity caused by the aperture of the probe is dominant in comparison to the deterioration in sensitivity caused by the reflectance loss on the probe surface. However, when the element size of the probe becomes 0.5 mm or less, the deterioration in sensitivity caused by the reflectance loss on the probe surface becomes dominant. Accordingly, particularly when the element size of the probe is small, the deterioration in sensitivity of the probe caused a problem by the reflectance loss on the probe surface.

This invention was devised in view of the foregoing problems. Thus, an object of this invention is to improve the resolution of the reconstructed image by correcting the reflectance loss at the interface of the object and the probe in Photoacoustic Tomography.

This invention provides an object information acquiring apparatus, comprising:

a probe for receiving, as a received signal, an acoustic wave which is generated within an object irradiated with light and propagates on an object surface; and a processor for generating object information, which is information based on an internal optical characteristic value of the object, by using intensity of the received signal, wherein the processor corrects the intensity of the received signal by performing amplification corresponding to a reflectance loss of the acoustic wave which is obtained according to an angle of the acoustic wave entering the probe.

This invention also provides an object information acquiring method, comprising:

a receiving step of a probe receiving, as a received signal, an acoustic wave which is generated within an object irradiated with light and propagates on an object surface; and a processing step of a processor generating object information, which is information based on an internal optical characteristic value of the object, by using intensity of the received signal, wherein, in the processing step, the intensity of the received signal is corrected by performing amplification corresponding to a reflectance loss of the acoustic wave which is obtained according to an angle of the acoustic wave entering the probe.

According to this invention, it is possible to improve the resolution of the reconstructed image by correcting the reflectance loss at the interface of the object and the probe in Photoacoustic Tomography.

Further features of this invention will become apparent from the following description of exemplary embodiments with reference to the attached drawings.

BRIEF DESCRIPTION OF THE DRAWINGS

FIG. 12 is a table showing the acoustic impedance of body tissues.

DESCRIPTION OF THE EMBODIMENTS

Figure 1:
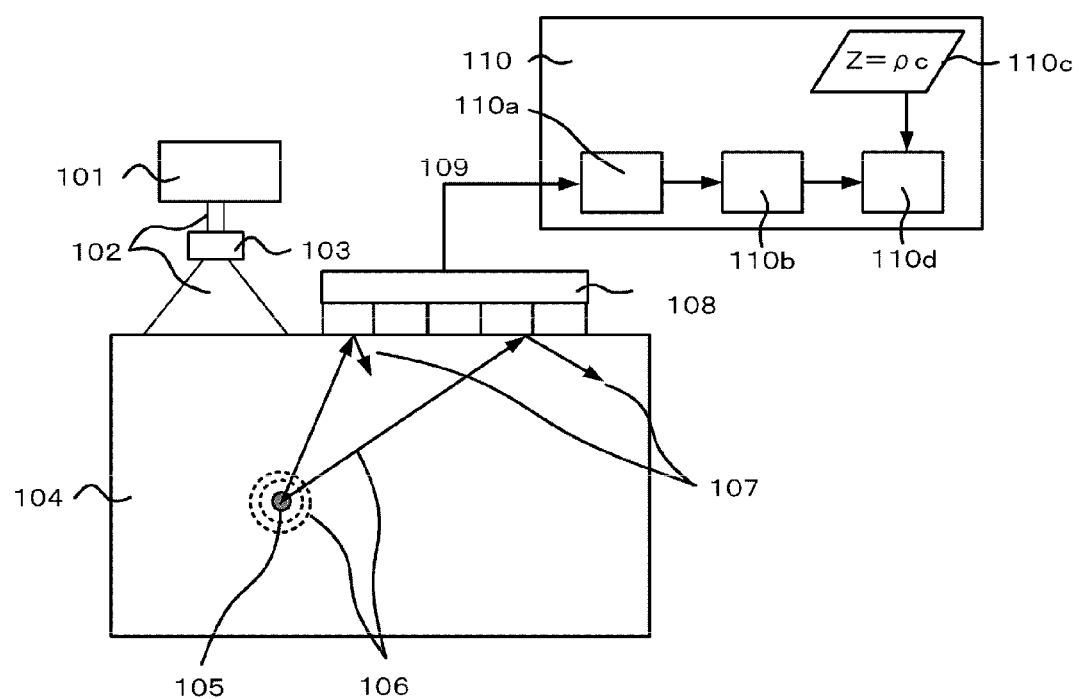
FIG. 1 is a diagram explaining the configuration of the photoacoustic signal acquiring apparatus of Embodiment 1.

A photoacoustic signal acquiring apparatus is now explained taking the object information acquiring apparatus of this invention as an example. Nevertheless, the target of this invention is not limited to the ensuing configuration. This invention can also be perceived as an object information acquiring method for realizing the following functions, or as an object information acquiring program for realizing the following functions by being supplied to an information processing device (computer or the like) via a network or a storage medium.

(Photoacoustic Signal Acquiring Apparatus)

The photoacoustic signal acquiring apparatus of this invention is an apparatus for generating information (object information) in the object based on calculation. The photoacoustic signal acquiring apparatus includes, as its basic hardware configuration, a light source, a probe as a receiver of acoustic waves, and a processor. Pulsed light emitted from the light source is irradiated to an object such as a living subject. When a part of the energy of light that propagated within the object is absorbed by a light absorber (sound source) such as blood, an acoustic wave (typically an ultrasound wave, and also referred to as photoacoustic wave or a photoacoustic ultrasound wave) is generated based on the thermal expansion of the light absorber. The acoustic wave is received by the probe and becomes an electric signal, and is transferred to the processor. The transferred electric signal is converted into optical characteristic value distribution information or the like in the object by the processor, and becomes object information. There is no particular limitation in the format of optical characteristic value distribution information, and may be arbitrarily determined to be two-dimensional, three-dimensional or the like depending on the purpose of measurement, device configuration, and so on. The generated object information may contain, in addition the optical characteristic value distribution and the absorption coefficient distribution, initial sound pressure distribution, substance concentration and oxygen saturation based thereon. In addition, it is also possible to include image data for forming and displaying images based on the foregoing information.

(Light Source)

In cases where the object is a living subject, irradiated from the light source is light of a specific wavelength that will be absorbed by a specific component among the components configuring the living subject. The light source may be provided integrally with the photoacoustic signal acquiring apparatus, or the light source may be separated and provided as a separate body. As the pulse width of the light source, a pulse width of roughly 10 nanoseconds is used in order to efficiently generate photoacoustic waves. While a laser is preferably used as the light source since significant power can be obtained, it is also possible to use a light-emitting diode, a flash lamp or the like in substitute for a laser. As the laser, solid-state laser, gas laser, dye laser, semiconductor laser and other lasers may be used. The timing, waveform and intensity of irradiation are controlled by a light source control unit not shown. Note that the light source control unit may also be integrated with the light source. In this invention, the wavelength of the used light source used is desirably a wavelength in which the light will propagate to the inside of the object. Specifically, in cases where the inside of the object is a living subject, a wavelength of 500 nm or more and 1200 nm or less is used.

(Probe)

A probe is a receiver for receiving acoustic waves that are generated and propagate on the object surface and in the object to which the pulsed light was irradiated. The probe converts the received acoustic wave into an electric signal (received signal), which is an analog signal. Any probe may be used including a probe which uses the piezoelectric phenomenon, a probe which uses the oscillation of light, a probe which uses the change in capacitance, or any other probe so as long as it can receive acoustic waves. If a component in which a plurality of receiving elements are disposed one-dimensionally or two-dimensionally is used as the probe, acoustic waves can be received simultaneously in various positions, and it is thereby possible to shorten the measuring time. When there is only one receiving element, it is also possible to perform scanning using the probe and receive the acoustic waves in various positions. Moreover, since a probe normally comprises an acoustic matching layer, the acoustic impedance, the acoustic velocity and the like of the probe to be used in the ensuing correction shall be the value of the acoustic matching layer on the outermost surface of the probe.

(Processor)

The processor is configured from an information processing device such as a computer and a circuit, and performs processing and operation of electric signals. The processor includes a conversion unit for converting the electric signal obtained with the probe from an analog signal into a digital signal. Desirably, the conversion unit can process a plurality of signals simultaneously. It is thereby possible to shorten the time required for forming an image. The converted digital signal is stored in a memory.

The processor additionally includes a correction operation unit for correcting the reflectance loss at the interface between the object and the probe based on the signals stored in the memory by using data and the like stored in a table. In addition, the processor generates object information such as optical characteristic value distribution, for instance, via back projection with a time domain based on the corrected signal.

The foregoing correction operation unit performs unique signal correction process in the image reconfiguration of arbitrary voxels or pixels; that is, processing of amplifying the intensity of the acoustic wave signal. The processor amplifies the signals with a great reflectance loss that enter the probe diagonally from the voxels or the pixels to a greater degree than the signals with a small reflectance loss that enter the probe perpendicularly from the voxels or the pixels. Consequently, the angle distribution of the sensitivity difference caused by the reflectance loss of acoustic waves on the probe surface is reduced, and deterioration in the resolution can be improved.

Figure 11A:
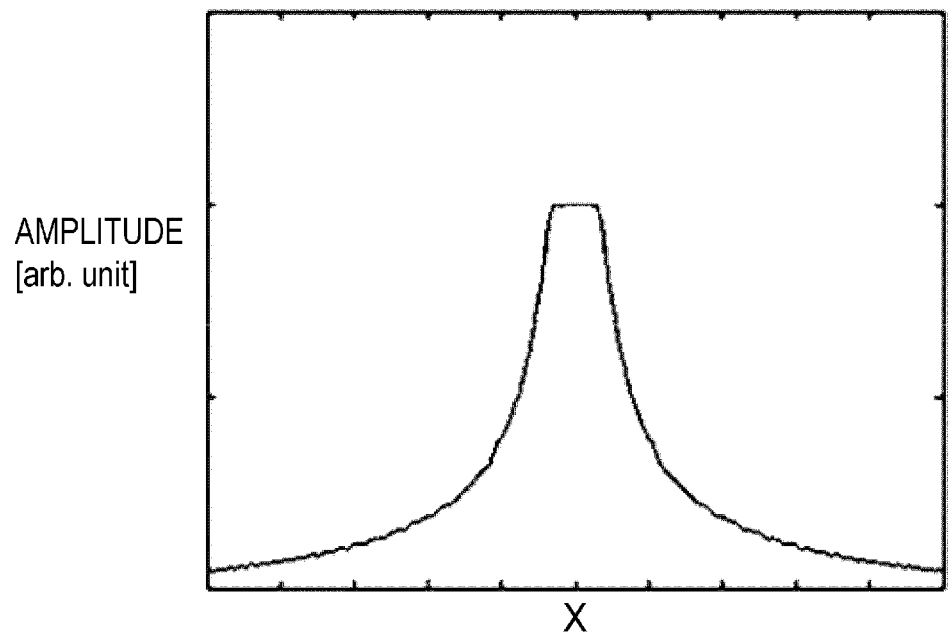
FIGS. 11A and 11B are diagrams schematically showing the intensity distribution in the cross section of the light absorber.
Figure 11B:
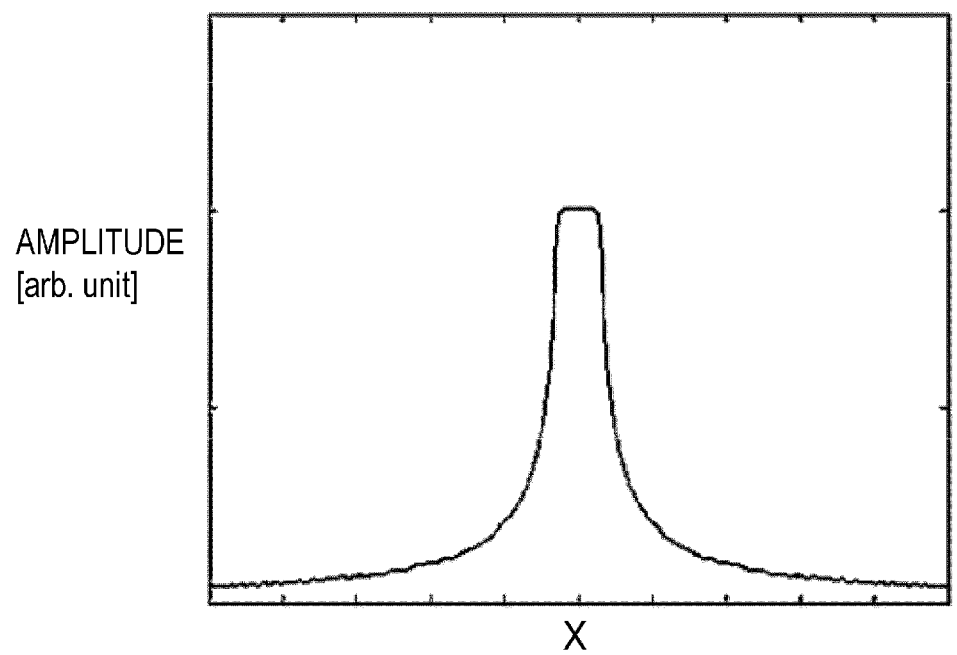

FIG. 11 is a diagram schematically showing how the intensity distribution of the light absorber in the object changes depending on the reflectance loss correction of this invention. FIG. 11A and FIG. 11B are diagrams schematically showing the intensity distribution in the cross section of the light absorber before and after the reflectance loss correction, respectively. In the diagrams, the horizontal axis represents the distance on the object, and the vertical axis represents the signal intensity. Accordingly, it can be seen that the resolution is improved by correcting the reflectance loss upon imaging the information in the object.

The respective embodiments of this invention are now explained with reference to the drawings.

Embodiment 1

FIG. 1 is a diagram explaining the configuration of the photoacoustic signal acquiring apparatus of Embodiment 1 of this invention.

A light source 101 is a titanium-sapphire laser excited with a double wave of a YAG laser, and generates a pulsed light 102. An irradiation optical system 103 is configured, for example, from a lens, a mirror, an optical fibre, and so on. The pulsed light 102 emitted from the light source 101 is guided by the irradiation optical system 103, and irradiated to the object 104. When a part of the energy of light that propagated inside the object 104 is absorbed by a light absorber 105 such as blood, an acoustic wave 106 is generated and propagates in the object 104. A part of the acoustic wave that propagated in the direction of the probe 108 becomes a reflected wave 107, and the remainder is received by the probe.

The probe 108 receives the acoustic wave 106 with the elements and converts the acoustic wave 106 into an analog electric signal, and sends the analog electric signal as a received signal 109 to the processor 110. The processor 110 is configured from a conversion unit 110a, a memory 110b, a first table 110c and a correction operation unit 110d. The conversion unit 110a amplifies the received signal 109 and performs A/D conversion to the received signal 109. The converted digital signal is stored in the memory 110b. The first table 110c stores at least two among acoustic impedance, density, and acoustic velocity of the object and the probe. However, the foregoing data may be changed by an operator via an input means. The correction operation unit 110d corrects the reflectance loss of the signals stored in the memory 110b based on the data input to the first table, and thereby performs image reconfiguration.

Figure 2A:
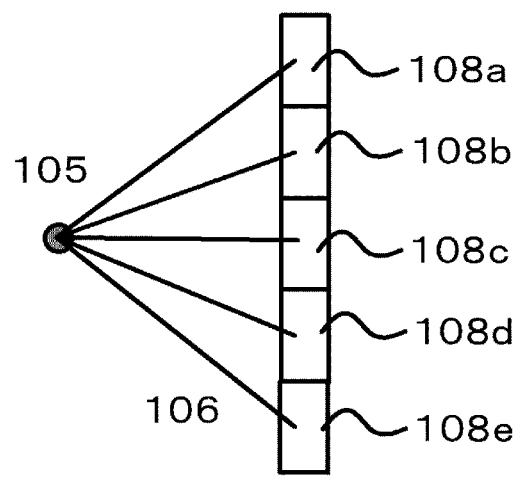
FIGS. 2A and 2B are diagrams explaining the positional relationship of the light absorber and the respective elements of the probe.

In order to explain the reflectance loss correction processing as the unique feature to be performed by the correction operation unit 110d, the received signal 109 is foremost explained with reference to FIG. 2. FIG. 2A is a diagram for explaining the positional relationship of the light absorber 105 and the respective elements 108a to 108e of the probe 108. Since the distance between the element 108c and the light absorber 105 is shorter in comparison to the distance between the element 108a and the light absorber 105, the time that the acoustic wave 106 is received by the element 108c will be faster than the time that the acoustic wave 106 is received by the element 108a. Accordingly, it can be seen that the signals of the timeframe to be received from the voxels or pixels to be subject to image reconfiguration are different according to the position of the elements in the probe.

Figure 2B:
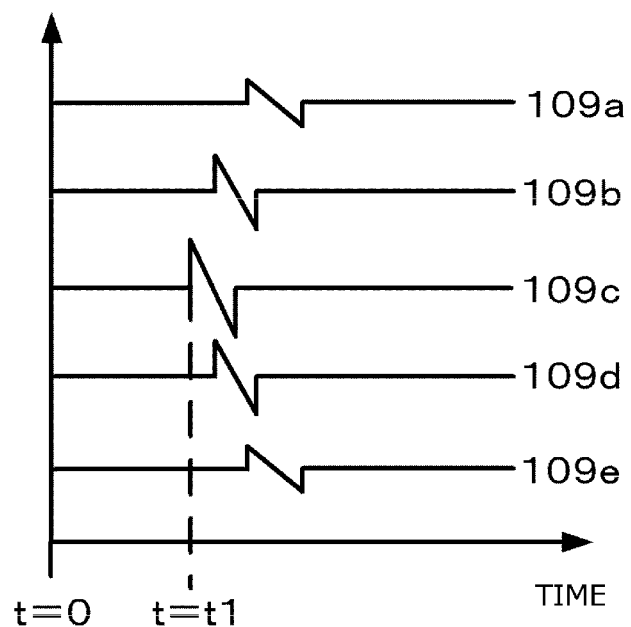

FIG. 2B is a diagram explaining the relationship of the propagating signals. t=0 is the base time. At t=t1, a signal 109c is received by the element 108c. Reference numerals 109a to 109e represent the signals of acoustic waves corresponding to the elements 108a to 108e. The received signal from the probe 108 is stored in the memory 110b via the conversion unit 110a.

Figure 3A:
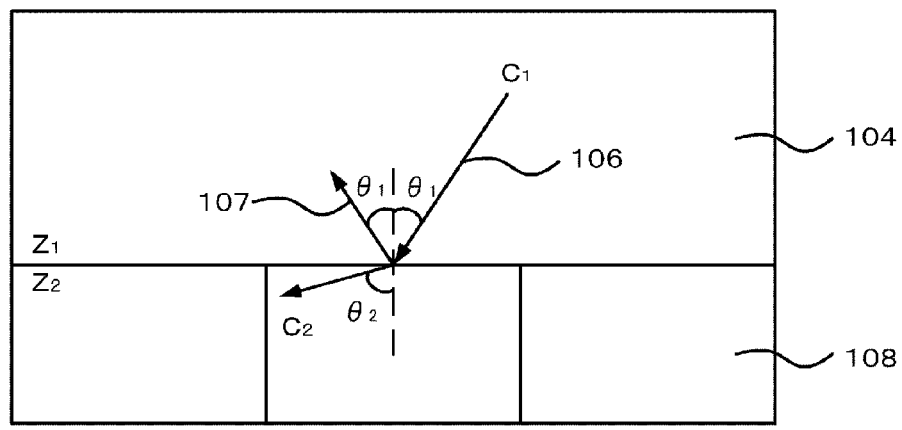
FIGS. 3A and 3B are diagrams explaining the reflection of the acoustic wave at the interface of the object and the probe.

FIG. 3A is a diagram schematically showing the state where the acoustic wave is reflected or transmitted at the interface of the object and the probe. In FIG. 3A, $Z_1$ is the acoustic impedance of the object 104, and $Z_2$ is the acoustic impedance (impedance of the acoustic matching layer) of the probe 108. Moreover, $\theta_1$ is the angle that the acoustic wave enters the probe, $\theta_2$ is the angle of the acoustic wave after entering the probe, $c_1$ is the acoustic velocity of the object, and $c_2$ is the acoustic velocity of the probe. A part of the acoustic wave 106 that propagated in the object becomes the reflected wave 107, and the remainder enters the probe.

Figure 3B:
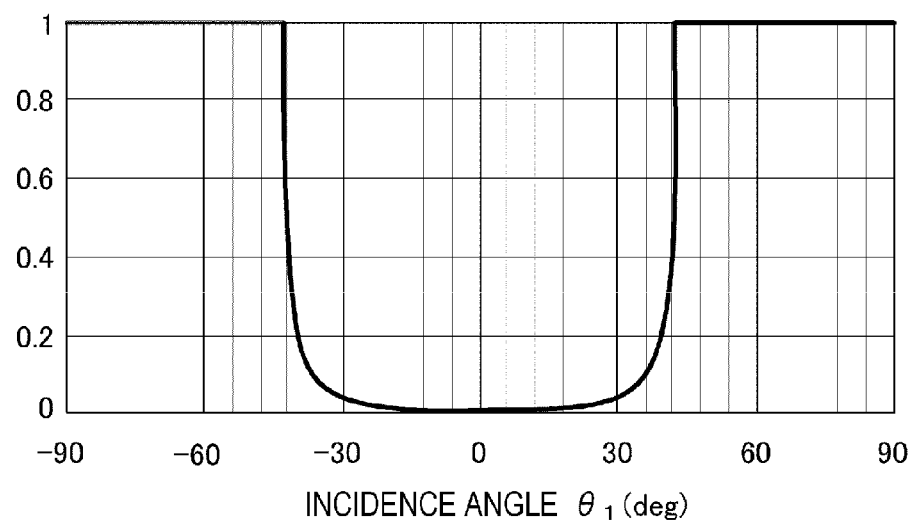

FIG. 3B is a graph showing the relationship of the angle $\theta_1$ that the acoustic wave enters the probe and the reflectance R. Here, the values related to the object and the probe were calculated as follows; namely, $Z_1 = 1.5 \times 10^6$ kg/m²s, $c_1 = 1500$ m/s, $Z_2 = 1.8 \times 10^6$ kg/m²s, and $c_2 = 2100$ m/s. As evident from FIG. 3B, the reflectance R is dependent on the angle $\theta_1$ that the acoustic wave enters the probe. Generally speaking, since the reflectance R will increase when the incidence angle $\theta_1$ of the acoustic wave is large, the receiving intensity of the acoustic wave will decrease as the incidence angle of the acoustic wave entering the element is large.

Figure 4:
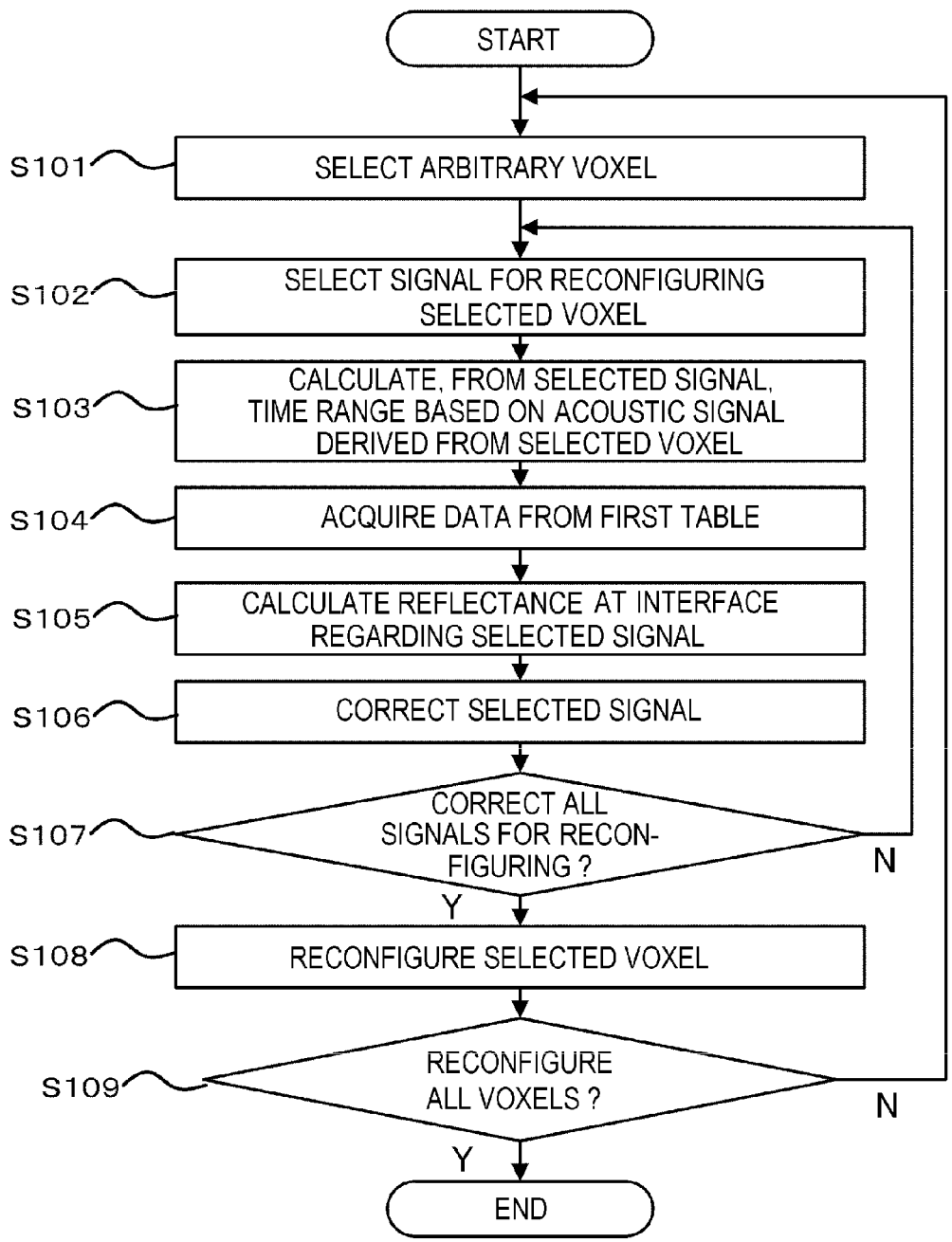
FIG. 4 is a flowchart of the correction processing of Embodiment 1.

The flow of the reflectance loss correction processing as the unique feature of this invention to be performed by the correction operation unit 110d is now explained with reference to FIG. 4. As the premises, let it be assumed that light from the light source is irradiated on a region to be subject to image reconfiguration within the object, and the acoustic wave generated thereby is being received by the respective elements of the probe. The image reconfiguration by the processor is started from the foregoing state.

(Step S101) The correction operation unit 110d selects arbitrary pixels or voxels from the region to be subject to image reconfiguration. Here, an example where the voxels are selected and a three-dimensional reconfiguration is to be performed is explained.

(Step S102) The correction operation unit 110d selects signals that can be used for reconfiguring the selected voxels. This process corresponds to selecting the element of the probe that can receive the acoustic wave for use in the reconfiguration based on the position of the voxels.

(Step S103) The correction operation unit 110d calculates the time range based on the acoustic wave derived from the voxels selected in step S101 among the selected signals based on the arrival time of the acoustic wave caused by the positional relationship shown in FIG. 2B.

(Step S104) The correction operation unit 110d acquires the data input in the first table 110c. Here, let it be assumed that the acoustic impedance and acoustic velocity of the object and the probe are input to the first table 110c.

(Step S105) The correction operation unit 110d obtains the angle from the positional relationship of the voxels and the elements, and thereafter calculates the reflectance R of the acoustic wave on the probe surface. The reflectance R is calculated based on Formulas (1) and (2) based on the data input to the first table 110c and the angle θ.

$$R = |(Z_1 \cos\theta_2 - Z_2 \cos\theta_1)/(Z_1 \cos\theta_2 + Z_2 \cos\theta_1)|^2 \quad (1)$$

$$\theta_2 = \sin^{-1}(c_2 \sin\theta_1/c_1) \quad (2)$$

Note that, while this embodiment used the acoustic impedance and the acoustic velocity of the object and the probe, since the acoustic impedance is the product of density and acoustic velocity, it will suffice so as long as at least two types of data among acoustic impedance, density, and acoustic velocity of the object are input to the first table 110c.

(Step S106) The correction operation unit 110d corrects the reflectance loss of the selected signals according to the incidence angle $\theta_1$ of the acoustic wave. The correction is performed by dividing the intensity of the signals of the corresponding time range by 1−R. However, the divisor is not limited to 1−R and, for instance, may also be 1−aR (wherein a is the coefficient of a≅1, and can be adjusted by the operator). When the acoustic wave is entirely reflected by the probe surface; that is, upon satisfying Formula (3) below, then R=1, and the signal in the foregoing case is not used in the image reconfiguration.

$$\theta_1 \geq \sin^{-1}(c_2/c_1) \quad (3)$$

Moreover, when R is close to 1, then 1−R becomes close to 0, and noise components will increase in addition to the signals. In the foregoing case, the upper limit of 1/(1−R) is set in advance, and the upper limit is used upon exceeding the upper limit. Moreover, measures may be taken so that a signal that exceeded the upper limit is not used in the image reconfiguration.

(Step S107) If the correction of all signals to be used in reconfiguring the selected voxels is not complete, the routine returns to S102 and the subsequent signal is corrected. If the correction is complete, the routine proceeds to the subsequent processing.

(Step S108) The correction operation unit 110d uses the corrected signal and reconfigures the image based on well-known methods such as FBP (Filtered Backprojection) or DELAY-AND-SUM.

Note that the timing of acquiring data from the first table, timing of selecting the signals to be used in the reconfiguration and calculating the reflectance at the interface, timing of performing reconfiguration and the like are not limited to the foregoing explanation. For example, it is also possible to acquire data from the first table immediately after the start of processing and manage such data in the memory, and use the data in subsequent calculations.

(Step S109) If the reconfiguration of all voxels in the region to be subject to image reconfiguration is not complete, the routine returns to S101 and the subsequent voxel is selected. Meanwhile, if the reconfiguration of all voxels in the intended region is complete, the processing is ended. The generated data is stored as object information. In addition, image correction processing or enhancement for achieving a favorable image display may also be performed.

Note that while this embodiment used Mathematical Formulas (1) and (2), the mathematical formula is not limited thereto, and an approximate equation may also be used. For example, as an approximate equation relative to Mathematical Formula (1), a formula of multiplying A (A≅1 and an adjustable coefficient) to the right side of Mathematical Formula (1) may also be used.

Moreover, while this embodiment illustrates an example of disposing a plurality of probes on the object surface, since the same effect can be obtained so as long as acoustic waves can be received, it is also possible to use a probe configured from one element and scan the object surface one-dimensionally or two-dimensionally.

According to the configuration of this embodiment described above, it is possible to reduce the difference in the receiving sensitivity in the front direction of the probe and the receiving sensitivity in the peripheral direction of the probe by correcting the reflectance loss of acoustic waves on the probe surface, and substantially broaden the aperture of the probe. Consequently, since received signals from various angles will contribute upon the image reconfiguration, the resolution can be improved.

Embodiment 2

Embodiment 1 explained a configuration of correcting, for each voxel or pixel, the reflectance loss on the probe surface based on the acoustic impedance and the acoustic velocity of the object stored in the first table 110c. In this embodiment, the method of correcting the reflectance loss by using an amplification factor for each receiving position corresponding all voxels or pixels in the image reconfiguration region is explained.

Figure 5A:
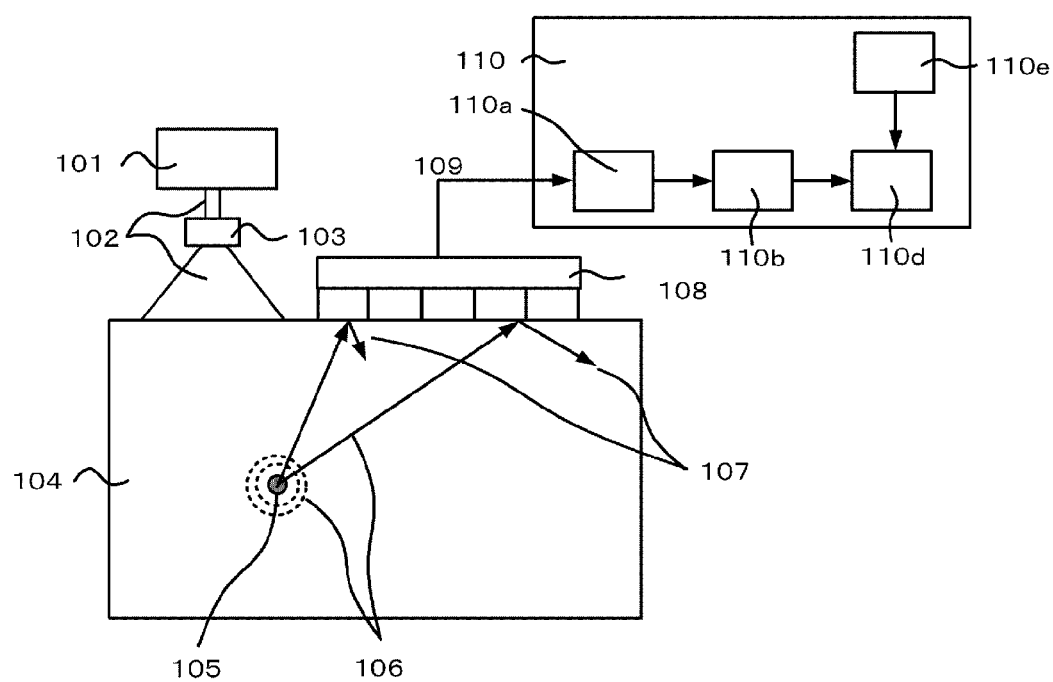
FIG. 5A is a diagram explaining the configuration of the photoacoustic signal acquiring apparatus of Embodiment 2.

FIG. 5A is a diagram schematically showing the configuration of the photoacoustic signal acquiring apparatus of this embodiment, and, since the configuration other than the processor 110 is the same as FIG. 1, the explanation thereof is omitted. A second table 110e of FIG. 5A is input with the amplification factor for each probe which is required for performing image reconfiguration to all voxels or pixels in the image reconfiguration region. In other words, the table 110e stores, for each angle that can be formed based on the device configuration, the amplification factor according to the positional relationship (distance and angle) of the element and the voxels or pixels to be processes. This amplification factor can be calculated by using Formula (1) of Embodiment 1 if the acoustic velocity and impedance of the object and the probe and the incidence angle of the acoustic wave are set in advance.

Figure 5B:
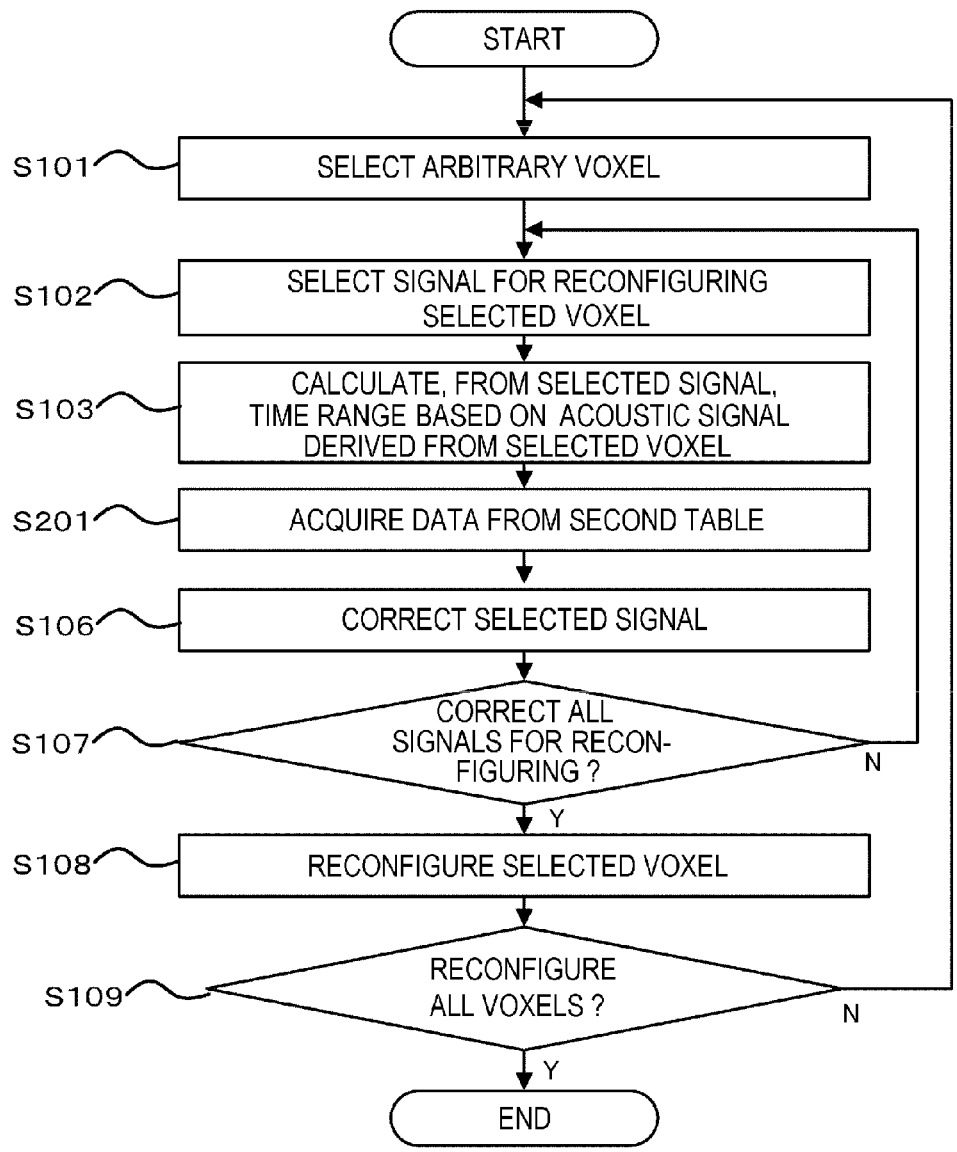
FIG. 5B is a flowchart of the correction processing of Embodiment 2.

The correction flow of this embodiment is now explained with reference to FIG. 5B. This flow differs only with respect to the point that step S201 is executed in substitute for steps S104 and S105 in FIG. 4 of Embodiment 1. Accordingly, the explanation of portions other than those which are different from Embodiment 1 will be brief.

(Steps S101 to S103) The correction operation unit 110d selects arbitrary voxels and calculates the time range of signals to be used for reconfiguring the selected voxels.

(Step S201) The correction operation unit 110d acquires correction data from the second table 110e. As described above, the correction data stores appropriate amplification factors based on the positional relationship of the selected voxels and the selected elements, and the reflectance obtained from characteristics such as the acoustic velocity and acoustic impedance of the object and the probe. Thus, as a result of performing amplification processing to the selected signals by using the foregoing amplification factor, the reflectance loss can be corrected. Note that it is also possible to simply store the reflectance in substitute for the amplification factor.

(Steps S106 to S109) The correction operation unit 110d reconfigures the voxels using the signals that were subject to amplification processing, and ends the processing upon completion of the reconfiguration of all voxels contained in the target region.

In the configuration of this embodiment described above also, the resolution is improved since the reflectance loss on the probe surface can be corrected. Since the amplification factor required for correcting the reflectance loss is known in advance for each voxel or pixel and can be easily acquired by referring to a table, the processing time can be shortened even more since there is no need to calculate formulas each time as with Embodiment 1.

Embodiment 3

This embodiment explained a configuration of correcting the deterioration in sensitivity caused by the aperture of the probe. The correction method is the same as the method of correcting the reflectance loss on the probe surface. In other words, information of the probe is stored in advance in the first table 110c. In addition, the correction operation unit 110d performs amplification processing to the signals of the time range to be received from the arbitrary voxels or pixels according to the incidence angle $\theta_1$ of the acoustic wave.

Specifically, when the elements of the probe are rectangular, the directionality $A(\theta)$ can be obtained with Formula (4) below. Here, k represents the wave number, a represents the element size of the probe, and $\theta$ represents the angle that the acoustic wave enters the probe. Based on this formula, the coefficient relative to the signal that enters perpendicularly in cases where the acoustic wave enters the element at an angle $\theta$ can be obtained.

$$A(\theta)=|\{\sin(ka\sin\theta)\}/(ka\sin\theta)| \quad (4)$$

Figure 6:
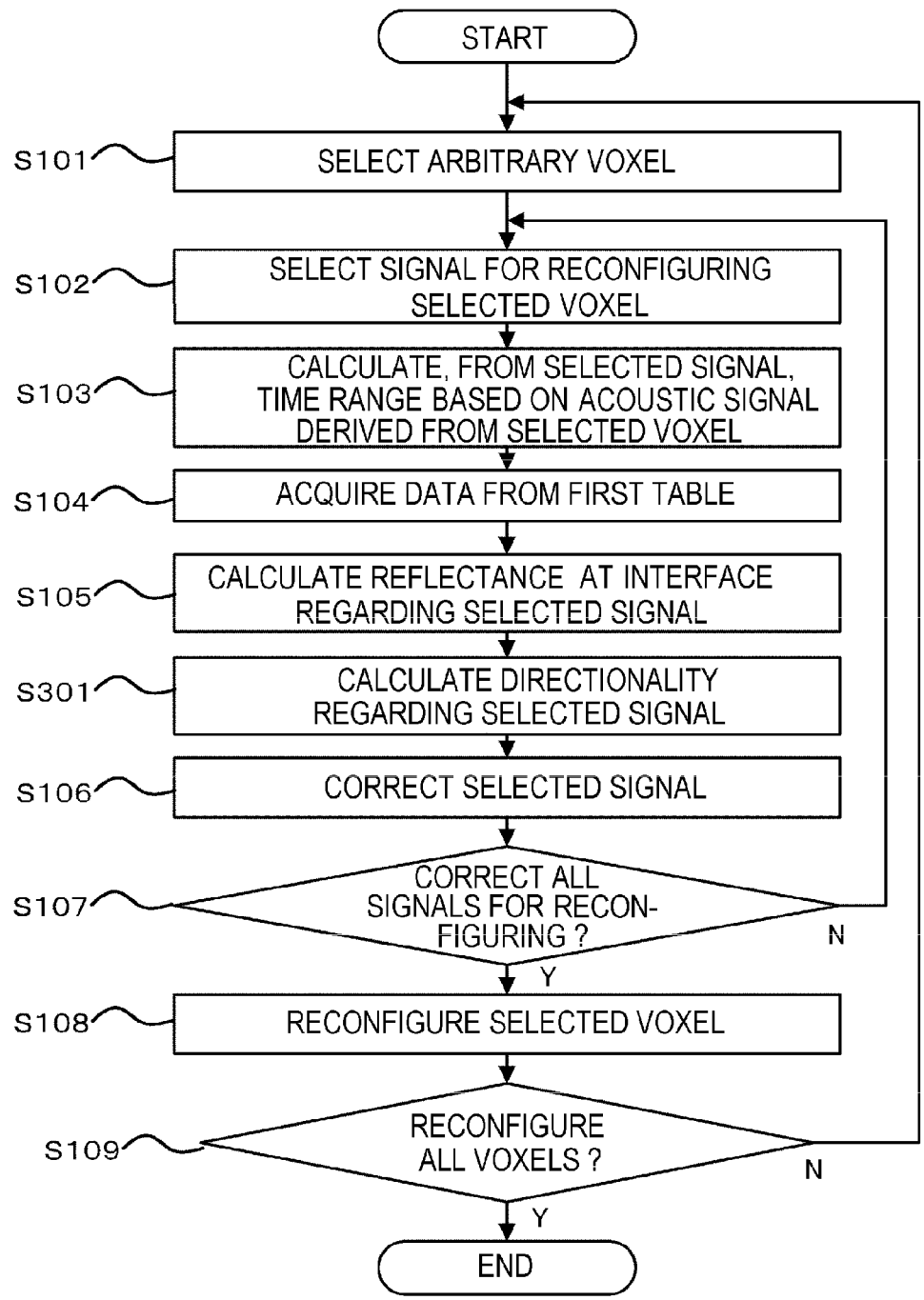
FIG. 6 is a flowchart of the correction processing of Embodiment 3.

The correction flow of this embodiment is now explained with reference to FIG. 6. Note that the explanation of portions other than those which are different from FIG. 4 of Embodiment 1 will be brief.

(Steps S101 to S103) The correction operation unit 110d selects the arbitrary voxels and calculates the time range of signals to be used for reconfiguring the selected voxels.

(Step S104) In this embodiment, the correction operation unit 110d acquires from the first table 110c, in addition the data (for instance, acoustic impedance and acoustic velocity) for obtaining the reflectance, data (for instance, wave number and element size) to be used in calculating the directionality.

(Step S105) The correction operation unit 110d obtains the angle from the positional relationship of the voxels and elements, and thereafter calculates the reflectance R of the acoustic wave on the probe surface based on Formulas (1) and (2).

(Step S301) In this embodiment, the correction operation unit 110d calculates the directionality $A(\theta)$ of the probe based on Formula (4).

(Step S106) In this embodiment, in addition the amplification processing based on the reflectance R, the correction operation unit 110d also performs the amplification processing based on the directionality $A(\theta)$ to correct the signals. The signals of the time range to be obtained are foremost corrected by dividing the intensity by 1−R, and additionally dividing the product by $A(\theta)$.

However, the value used for correcting the aperture is not limited to $A(\theta)$, and, for instance, $bA(\theta)$ (wherein b is a coefficient of b≅1, can be arbitrarily adjusted by the operator) may also be used. Moreover, when the element size is large, an upper limit may be set to directionality $1/A(\theta)$ in order to avoid the influence of noise from becoming too great.

(Step S107 to S109) The correction operation unit 110d reconfigures the voxels using the signals that were subject to amplification processing, and ends the processing upon completion of the reconfiguration of all voxels contained in the target region. Information of the object in the region is thereby imaged.

According to the configuration of this embodiment described above, a more accurate image can be obtained since the directionality of the probe is corrected in addition to the reflectance loss of the acoustic wave on the probe surface being corrected.

Note that, rather than performing calculations each time using Formula (4), it is also possible to measure the directionality of the probe in advance and store the result in the first table 110c, and use such measured directionality as needed.

Embodiment 4

When it is desirable to fix and measure an object or perform scanning with the probe on the object, the object may be held with a holding plate. In the foregoing case, the acoustic wave will be received by the probe via the holding plate that is compressing the object. Consequently, since reflectance loss of the acoustic wave will arise at the interface of the object and the holding plate and at the interface of the holding plate and the probe, there is an additional problem in that an accurate image cannot be obtained.

Thus, this embodiment explains a configuration example where, upon holding the object with the holding plate, the reflectance loss of the acoustic wave at the interface of the object and the holding plate and at the interface of the holding plate and the probe is corrected in order to obtain an accurate image.

Figure 7:
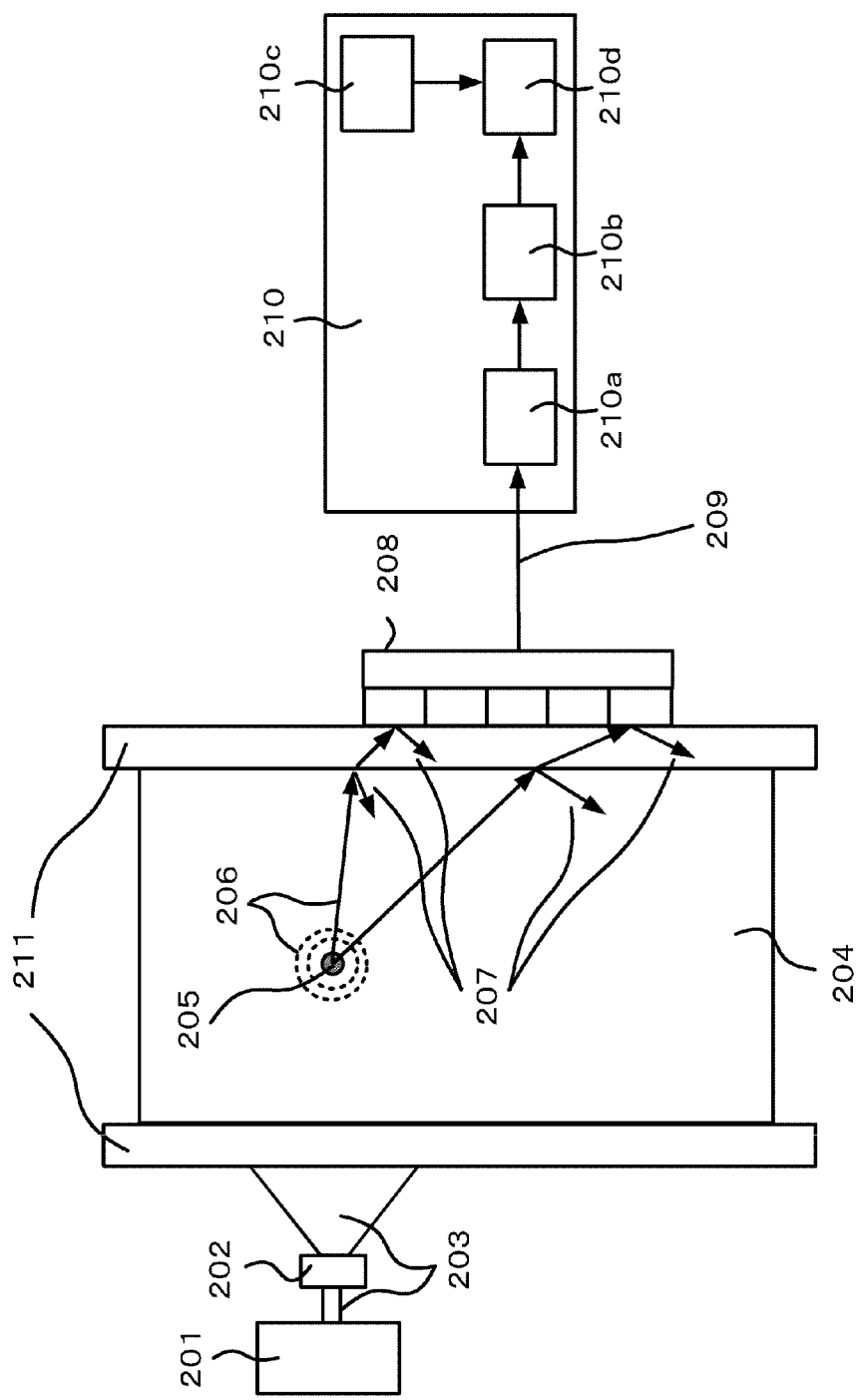
FIG. 7 is a diagram explaining the configuration of the photoacoustic signal acquiring apparatus of Embodiment 4.

FIG. 7 shows a configuration of the photoacoustic signal acquiring apparatus according to Embodiment 3 of this invention. The photoacoustic signal acquiring apparatus comprises a light source 201, an irradiation optical system 202 such as a mirror, a probe 208, and a processor 210. The same components as Embodiment 1 may be used for the foregoing components.

The photoacoustic signal acquiring apparatus of this embodiment comprises a holding plate 211. The holding plate 211 may be fixed or movable. Otherwise, when there are two holding plates, one may be fixed while the other one made to be movable so as to compress and hold the object at an appropriate thinness. The holding plate on the light source side is preferably made of polycarbonate or acrylic which transmits light easily, and the holding plate on the probe side is preferably made of polymethylpentene which easily transmits acoustic waves.

In this embodiment, the reflectance loss of the acoustic wave at the interface of the object and the holding plate and at the interface of the holding plate and the probe is corrected. Thus, the first table 210c stores at least two among acoustic impedance, density, and acoustic velocity data related to the object, holding plate and probe.

As the correction method, after obtaining the reflectance with the calculation method described in Embodiment 1, the processing of amplifying the signal intensity by dividing the signal intensity by the reflectance may be applied to the respective interfaces.

Moreover, as with Embodiment 2, the processor 210 may also include a second table 210e (not shown) containing the amplification factor of each element of the probe corresponding to all voxels or pixels in the image reconfiguration region.

According to the configuration of this embodiment explained above, even in cases where the object is held by the holding plate, the reflectance loss of the acoustic wave at the interface of the object and the holding plate and at the interface of the holding plate and the probe is corrected, and it is thereby possible to obtain an image with improved resolution.

Embodiment 5

While the reflectance loss of the acoustic wave at the interface of the object and the holding plate and at the interface of the holding plate and the probe was corrected in Embodiment 4, if the attenuation of the acoustic wave in the holding plate is also obtained and the attenuation is corrected, information in the object can be more accurately imaged. This embodiment explained this method with reference to FIG. 8.

Figure 8:
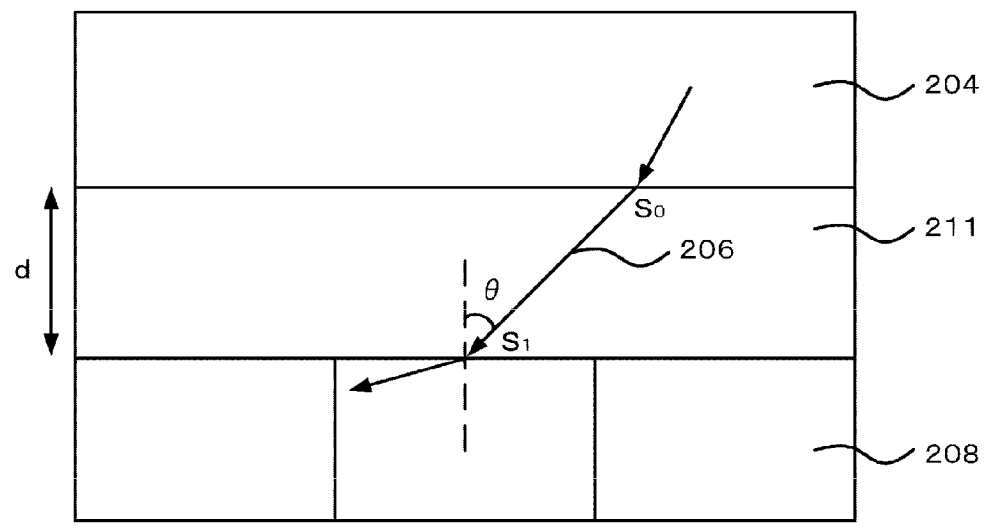
FIG. 8 is a diagram explaining the propagation of the acoustic wave in the holding plate.

In FIG. 8, reference numeral 204 represents an object, reference numeral 211 represents a holding plate, reference numeral 208 represents a probe, and the acoustic wave 206 enters the probe from the object via the holding plate. When the thickness of the holding plate is d, the absorption coefficient is $\mu$, and the angle that the acoustic wave enters the probe from the holding plate is $\theta$, the relationship of the intensity $S_0$ of the acoustic wave immediately after entering the holding plate and the intensity $S_1$ of the acoustic wave immediately before being emitted from the holding plate will be as shown in Formula (5).

$$S_1 = S_0 \exp(-\mu d/\cos \theta) \qquad (5)$$

Accordingly, in Embodiment 4, upon performing the correction of dividing the signal intensity by the reflectance, if the signal intensity is simultaneously divided by $\exp(-\mu d/\cos \theta)$, it is possible to correct the attenuation of the acoustic wave in the holding plate according to the attenuation rate, and thereby acquire a more accurate image.

According to the configuration of this embodiment explained above, since the attenuation of the acoustic wave in the holding plate is corrected, it is possible to obtain a more accurate image. Note that while this embodiment used Mathematical Formula (5), the mathematical formula is not limited thereto, and an approximate equation may also be used.

Embodiment 6

While Embodiments 1 to 5 used an estimate value as the acoustic impedance of the object, the acoustic impedance may differ for each object. Accordingly, in order to obtain a more accurate image, it is desirable to actually measure the acoustic impedance for each object and correct the reflectance loss of the acoustic wave by using the result thereof. This embodiment explains a configuration example of actually measuring the acoustic impedance of the object and correcting the reflectance loss based on the result of such actual measurement.

Figure 9A:
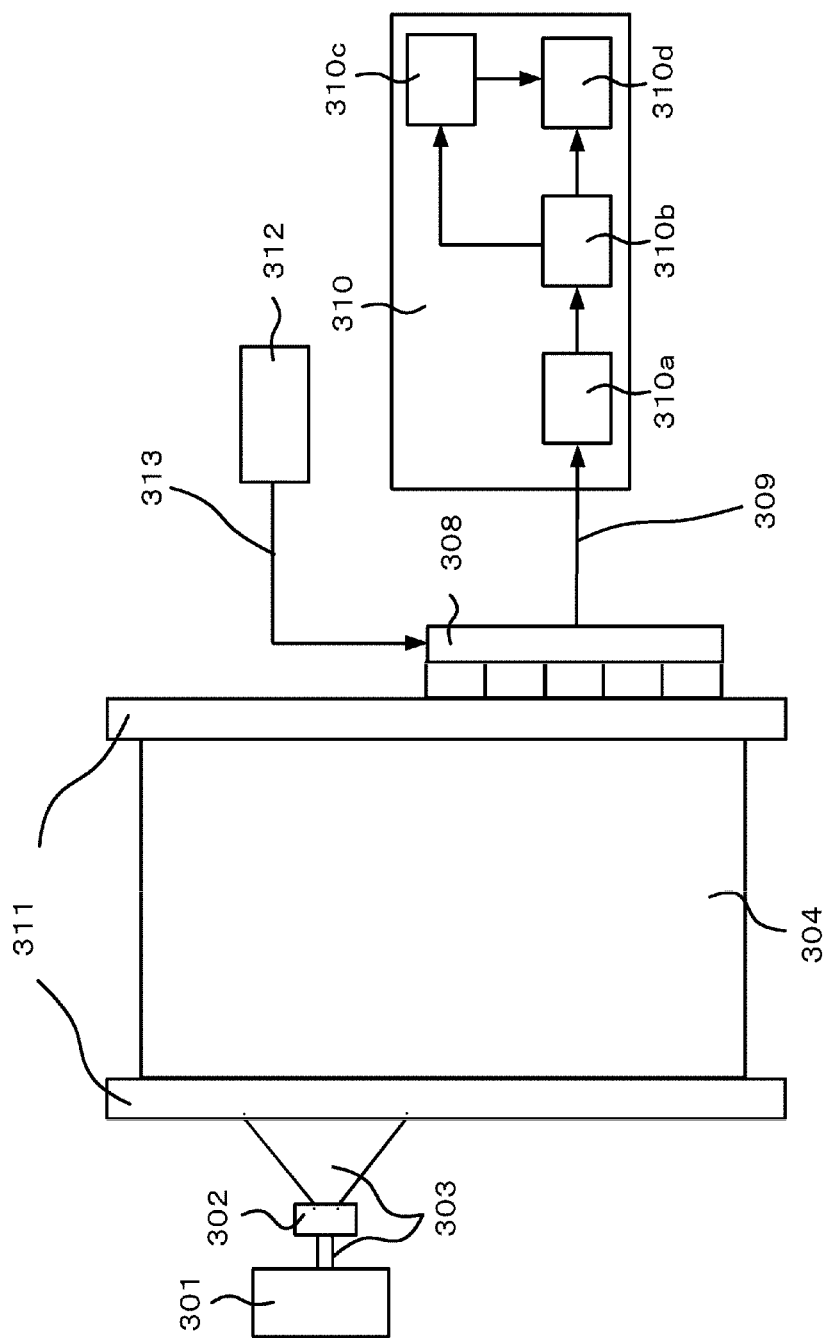
FIG. 9A is a diagram explaining the configuration of the photoacoustic signal acquiring apparatus of Embodiment 6.

FIG. 9A is a diagram showing a configuration of the photoacoustic signal acquiring apparatus according to this embodiment. The photoacoustic signal acquiring apparatus comprises a light source 301, an irradiation optical system 302 such as a mirror, a probe 308, a processor 310, and a holding plate 311. The same components used in the foregoing embodiments may also be used as the foregoing components. Moreover, the photoacoustic signal acquiring apparatus in this embodiment comprises a transmitting circuit 312 for transmitting ultrasound waves from the object 304 to the probe 308. As a result of a transmitting signal 313 being transmitted from the transmitting circuit 312 to the probe 308, ultrasound waves are transmitted from the probe 308.

Figure 9B:
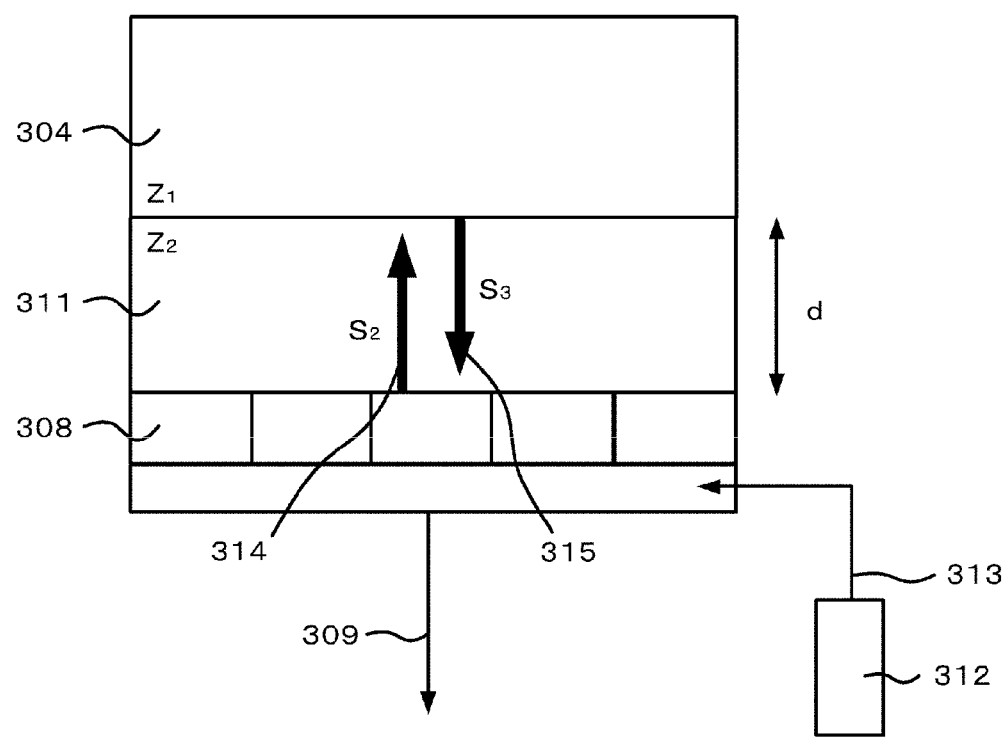
FIG. 9B is a diagram explaining the method of measuring the acoustic impedance of the object of Embodiment 6.
Figure 10:
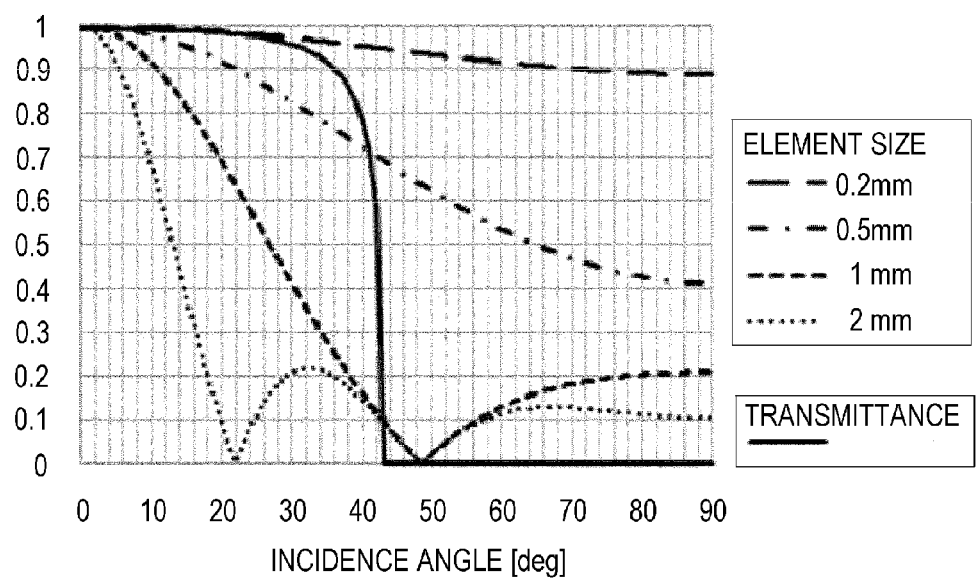
FIG. 10 is a diagram explaining the incidence angle of the acoustic wave upon entering the probe.

The method of measuring the acoustic impedance of the object is now explained with reference to FIG. 9B. Foremost, a pulse transmission wave 314 of a certain intensity is caused to enter from the probe toward the holding plate and the air interface in a state where the holding plate is not holding the object and is in contact with air. This ultrasound wave intensity shall be $S_2$. Since the ultrasound wave is substantially reflected by the holding plate and air interface in its entirety, an ultrasound wave (first reflected wave) of an intensity that is substantially the same as the incoming ultrasound wave intensity $S_2$ is received by the probe.

Subsequently, the ultrasonic wave is transmitted in a state where the holding plate is holding the object. At base time t=0, the same pulse transmission wave 314 of intensity $S_2$ is caused to enter the object 304 from the probe 308 via the holding plate 311. Consequently, the incoming pulse transmission wave 314 is reflected at the interface of the object and the holding plate (second reflected wave).

Here, if the acoustic velocity c in the holding plate is known, it is possible to calculate the time (t=2d/c) required for the ultrasound wave to reciprocate the holding plate 311 having the thickness d. Thus, the intensity $S_3$ of the pulse reflected wave 315 that reaches the probe when time t elapses from the base time is detected. The reflectance $R=S_3/S_2$ can thereby be calculated.

When the acoustic impedance of the object is $Z_1$, and the acoustic impedance of the holding plate is $Z_2$, the relationship of the reflectance R and $Z_1$, $Z_2$ will be as shown in Formula (6).

$$R=|(Z_2-Z_1)/(Z_2+Z_1)|^2 \quad (6)$$

Accordingly, if the acoustic impedance $Z_2$ of the holding plate is known, it is possible to measure the reflectance R, and thereafter calculate the acoustic impedance $Z_1$ of the object 304. The calculated acoustic impedance of the object 304 is stored in the table 310c.

Subsequently, the image reconfiguration according to the method described in Embodiment 1 is performed based on the stored acoustic impedance of the object 304.

According to the configuration of this embodiment explained above, since the acoustic impedance of the object can be actually measured, the reflectance loss is corrected more accurately, and it is possible to obtain an image with improved resolution.

Note that, without limitation to the first table 310c during the correction, the second table containing the correction data of the respective elements of the probe corresponding to all voxels or pixels in the image reconfiguration region may also be used. In the foregoing case, after obtaining the acoustic impedance of the object 304 with the method of this embodiment, data to be used for the correction is calculated based on the positional relationship of the voxels or pixels and the elements of the probe. In addition, the correction data is stored in the second table 310e, and used upon performing the image reconfiguration.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An object information acquiring apparatus comprising:
a probe configured to receive an acoustic wave which is generated from an object irradiated with light and output a time-series signal; and
a processor configured to obtain object information at a voxel or pixel by using the time-series signal,
wherein said processor is configured to obtain the object information at the voxel or the pixel without using an intensity of the time-series signal which is derived from the voxel or the pixel when an incident angle of the acoustic wave, generated from the voxel or pixel, entering the probe exceeds an upper limit.

2. The apparatus according to claim 1,
wherein said processor is configured to correct an intensity of the time-series signal derived from the voxel or the pixel, by performing correction corresponding to a reflectance loss of the acoustic wave which is obtained according to an incident angle of the acoustic wave entering said probe, and
wherein said processor is configured to obtain the object information at the voxel or the pixel based on the corrected intensity.

3. The apparatus according to claim 2, wherein, when a reflectance upon the acoustic wave entering said probe is R and a coefficient is a, said processor is configured to perform the correction by dividing the intensity derived from the voxel or the pixel, of the time-series signal, by (1−aR).

4. The apparatus according to claim 3, further comprising:
a first table storing at least two among acoustic impedance, density and acoustic velocity for the object and said probe,
wherein said processor is configured to obtain the reflectance by performing calculation based on information stored in said first table.

5. The apparatus according to claim 2, further comprising:
a second table storing a correction factor to be used for correcting the intensity of the received signal according to the incident angle of the acoustic wave entering said probe,
wherein said processor is configured to correct, by the correction factor, the intensity derived from the voxel or the pixel, of the time-series signal.

6. The apparatus according to claim 1, wherein said processor is configured to correct the intensity derived from the voxel or the pixel, of the received signal by performing correction corresponding to a sensitivity of said probe for the acoustic wave which deteriorates according to an incident angle of the acoustic wave entering said probe.

7. The apparatus according to claim 2, wherein said processor is configured to correct the intensity derived from the voxel or the pixel, of the received signal by performing correction corresponding to a sensitivity of said probe for the acoustic wave which deteriorates according to the incident angle of the acoustic wave entering said probe and in addition performing correction corresponding to the reflectance loss of the acoustic wave.

8. The apparatus according to claim 1, further comprising:
a holding member configured to hold the object,
wherein said probe is configured to receive the acoustic wave from the object via said holding member, and
wherein said processor is configured to correct the intensity derived from the voxel or the pixel, of the time-series signal by performing correction corresponding to a reflectance loss obtained according to an incident angle of the acoustic wave entering said holding member.

9. The apparatus according to claim 2, further comprising:
a holding member configured to hold the object,
wherein said probe is configured to receive the acoustic wave from the object via said holding member, and
wherein said processor is configured to correct the intensity derived from the voxel or the pixel, of the time-series signal by performing correction corresponding to a reflectance loss obtained according to an incident angle of the acoustic wave entering said holding member in addition to performing correction corresponding to the reflectance loss of the acoustic wave which is obtained according to the incident angle of the acoustic wave entering said probe.

10. The apparatus according to claim 1, further comprising:
a holding member configured to hold the object,
wherein said probe is configured to receive the acoustic wave from the object via said holding member, and
wherein said processor is configured to correct the intensity derived from the voxel or the pixel, of the time-series signal by performing correction corresponding to an attenuation rate of the acoustic wave in said holding member.

11. The apparatus according to claim 2, further comprising:
a holding member configured to hold the object,
wherein said probe is configured to receive the acoustic wave from the object via said holding member, and
wherein said processor is configured to correct the intensity derived from the voxel or the pixel, of the time-series signal by performing correction corresponding to an attenuation rate of the acoustic wave in said holding member in addition to performing correction corresponding to the reflectance loss of the acoustic wave which is obtained according to the incident angle of the acoustic wave entering said probe.

12. The apparatus according to claim 9,
wherein said probe is configured to transmit an acoustic wave to the holding member in a state in which said holding member is not holding the object and receives a first reflected wave, and thereafter transmits an acoustic wave to said holding member in a state in which said holding member is holding the object and receives a second reflected wave, and
wherein said processor is configured to obtain the reflectance loss by using intensities of the first and second reflected waves and an acoustic impedance of the object obtained from an acoustic impedance of said holding member.

13. The apparatus according to claim 11,
wherein said probe is configured to transmit an acoustic wave to the holding member in a state in which said holding member is not holding the object and receives a first reflected wave, and thereafter transmit an acoustic wave to said holding member in a state in which said holding member is holding the object and receive a second reflected wave, and
wherein said processor is configured to obtain the reflectance loss by using intensities of the first and second reflected waves and an acoustic impedance of the object obtained from an acoustic impedance of said holding member.

14. The apparatus according to claim 1,
wherein said processor is configured to correct an intensity of the time-series signal, derived from the voxel or the pixel based on an incident angle of the acoustic wave entering said probe, at least two among acoustic impedance, density, and acoustic velocity for the object, and at least two among acoustic impedance, density, and acoustic velocity for said probe, and
wherein said processor is configured to obtain the object information at the voxel or the pixel based on the corrected intensity.

15. The apparatus according to claim 1, wherein the upper limit is a total reflection angle of the acoustic wave for said probe.

16. A method for obtaining object information at a voxel or a pixel based on an intensity derived from the voxel or the pixel, of a time-series signal obtained by receiving, by means of a probe, an acoustic wave which is generated from an object irradiated with light comprising:
obtaining object information at the voxel or the pixel without using an intensity of the time-series signal which is derived from the voxel or the pixel when an incident angle of the acoustic wave, generated from the voxel or pixel, entering the probe exceeds an upper limit.

17. The method according to claim 16, further comprising:
correcting the intensity of the time-series signal derived from the voxel or the pixel, by performing correction corresponding to a reflectance loss of the acoustic wave which is obtained according to an incident angle of the acoustic wave entering the probe, and
obtaining the object information at the voxel or the pixel based on the corrected intensity obtained in said correcting step.

18. The method according to claim 16, further comprising:
correcting an intensity, of the time-series signal, derived from the voxel or the pixel based on an incident angle of the acoustic wave entering the probe, at least two among acoustic impedance, density, and acoustic velocity for the object, and at least two among acoustic impedance, density, and acoustic velocity for said probe, and
obtaining the object information at the voxel or the pixel based on the corrected intensity.

19. The method according to claim 16, wherein the upper limit is a total reflection angle of the acoustic wave for said probe.

20. The method according to claim 17, wherein, when a reflectance upon the acoustic wave entering said probe is R and a coefficient is a, the correction is performed by dividing the intensity derived from the voxel or the pixel, of the time-series signal, by $(1-aR)$.

21. The apparatus according to claim 1, wherein the incident angle is an angle between a surface of the probe and a line connecting the probe and the voxel or pixel.

22. The method according to claim 16, wherein the incident angle is an angle between a surface of the probe and a line connecting the probe and the voxel or pixel.

23. The apparatus according to claim 1, further comprising a light irradiation unit configured to irradiate the object with the light.

24. An object information acquiring apparatus comprising:
a probe configured to receive an acoustic wave which is generated from an object irradiated with light and output a time-series signal; and
a processor configured to obtain object information at a voxel or pixel by using the time-series signal,
wherein said processor is configured to obtain the object information at the voxel or the pixel by selectively using an intensity of the time-series signal which is derived from the voxel or the pixel in the case that an incident angle of the acoustic wave, generated from the voxel or pixel, entering the probe is below an upper limit.

25. The apparatus according to claim 24, wherein said processor is configured to correct an intensity of the time-series signal derived from the voxel or the pixel, by performing correction corresponding to a reflectance loss of the acoustic wave which is obtained according to an incident angle of the acoustic wave entering said probe, and wherein said processor is configured to obtain the object information at the voxel or the pixel based on the corrected intensity.

26. The apparatus according to claim 25, wherein, when a reflectance upon the acoustic wave entering said probe is R and a coefficient is a, said processor is configured to perform the correction by dividing the intensity derived from the voxel or the pixel, of the time-series signal, by (1−aR).

27. The apparatus according to claim 24, wherein said processor is configured to correct an intensity of the time-series signal, derived from the voxel or the pixel based on an incident angle of the acoustic wave entering said probe, at least two among acoustic impedance, density, and acoustic velocity for the object, and at least two among acoustic impedance, density, and acoustic velocity for said probe, and wherein said processor is configured to obtain the object information at the voxel or the pixel based on the corrected intensity.

28. The apparatus according to claim 24, wherein the upper limit is a total reflection angle of the acoustic wave for said probe.

29. The apparatus according to claim 24, wherein the incident angle is an angle between a surface of the probe and a line connecting the probe and the voxel or pixel.

30. The apparatus according to claim 24, further comprising a light irradiation unit configured to irradiate the object with the light.

31. A method for obtaining object information at a voxel or a pixel based on an intensity derived from the voxel or the pixel, of a time-series signal obtained by receiving, by means of a probe, an acoustic wave which is generated from an object irradiated with light comprising:

obtaining object information at the voxel or the pixel by selectively using an intensity of the time-series signal which is derived from the voxel or the pixel in the case that an incident angle of the acoustic wave, generated from the voxel or pixel, entering the probe is below an upper limit.

32. The method according to claim 31, further comprising:

correcting the intensity of the time-series signal derived from the voxel or the pixel, by performing correction corresponding to a reflectance loss of the acoustic wave which is obtained according to an incident angle of the acoustic wave entering the probe, and obtaining the object information at the voxel or the pixel based on the corrected intensity obtained in said correcting step.

33. The method according to claim 32, wherein, when a reflectance upon the acoustic wave entering said probe is R and a coefficient is a, the correction is performed by dividing the intensity derived from the voxel or the pixel, of the time-series signal, by (1−aR).

34. The method according to claim 31, further comprising:

correcting an intensity, of the time-series signal, derived from the voxel or the pixel based on an incident angle of the acoustic wave entering the probe, at least two among acoustic impedance, density, and acoustic velocity for the object, and at least two among acoustic impedance, density, and acoustic velocity for said probe, and obtaining the object information at the voxel or the pixel based on the corrected intensity.

35. The method according to claim 31, wherein the upper limit is a total reflection angle of the acoustic wave for said probe.

36. The apparatus according to claim 31, wherein the incident angle is an angle between a surface of the probe and a line connecting the probe and the voxel or pixel.

* * * * *